United States Patent
Lampropoulos et al.

(10) Patent No.: US 9,233,226 B2
(45) Date of Patent: Jan. 12, 2016

(54) DRAINAGE CATHETER WITH PIG-TAIL STRAIGHTENER

(75) Inventors: Fred P. Lampropoulos, Salt Lake City, UT (US); Nicholas Gerald Accisano, III, Howell, NJ (US); Louise Marini, Middletown, NJ (US)

(73) Assignee: Merit Medical Systems, Inc., South Jordan, UT (US)

( * ) Notice: Subject to any disclaimer, the term of this patent is extended or adjusted under 35 U.S.C. 154(b) by 1489 days.

(21) Appl. No.: 11/507,777

(22) Filed: Aug. 22, 2006

(65) Prior Publication Data

US 2008/0097394 A1 Apr. 24, 2008

(51) Int. Cl.
| | | |
|---|---|---|
| A61M 25/00 | (2006.01) | |
| A61M 25/01 | (2006.01) | |
| A61M 27/00 | (2006.01) | |
| A61M 25/06 | (2006.01) | |

(52) U.S. Cl.
CPC ....... *A61M 25/0147* (2013.01); *A61M 25/0041* (2013.01); *A61M 27/00* (2013.01); *A61M 2025/0163* (2013.01); *A61M 2025/0681* (2013.01)

(58) Field of Classification Search
CPC ..................... A61M 25/04; A61M 2025/0163; A61M 2025/09125
USPC ............................... 604/264, 164.01, 164.11, 604/170.01–170.03, 523, 275, 279, 525, 604/530
See application file for complete search history.

(56) References Cited

U.S. PATENT DOCUMENTS

| | | | |
|---|---|---|---|
| 604,617 | A | 5/1898 | Hoxie |
| 1,207,479 | A | 12/1916 | Bisgaard |
| 2,051,247 | A | 8/1936 | DeHaes |
| 3,315,592 | A | 4/1967 | Lems |
| 3,513,848 | A | 5/1970 | Winston et al. |
| 3,798,687 | A | 3/1974 | Stevens |
| 3,924,633 | A | 12/1975 | Cook et al. |
| 4,206,910 | A | 6/1980 | Biesemeyer |
| 4,573,981 | A | 3/1986 | McFarlane |
| 4,586,923 | A | 5/1986 | Gould et al. |
| 4,643,720 | A | 2/1987 | Lanciano |
| 4,738,667 | A * | 4/1988 | Galloway .............. A61M 25/04 604/530 |

(Continued)

FOREIGN PATENT DOCUMENTS

| | | |
|---|---|---|
| EP | 0609020 | 8/1994 |
| WO | WO 99/16355 | 4/1999 |

(Continued)

OTHER PUBLICATIONS http://www.pbn-medicals.com/Factsheets/Radiology/SkaterSingleStepDrainageCath.pdf.

(Continued)

*Primary Examiner* — Phillip Gray
(74) *Attorney, Agent, or Firm* — Stoel Rives LLP (57) ABSTRACT

A drainage catheter, including a catheter tube body that can have a pig-tail loop in a distal end, a rigid member configured to be placed inside of the catheter, a pig-tail straightening sleeve configured to move axially along the tube body, the sleeve having a lip formed on an end of the sleeve, the lip being configured to be positioned towards the distal end of the tube body, thereby straightening the catheter tube body and facilitating entry of the rigid member into the catheter tube body when the pig-tail straightening sleeve is positioned to straighten the catheter tube body.

13 Claims, 5 Drawing Sheets

(56) References Cited

U.S. PATENT DOCUMENTS

| | | | |
|---|---|---|---|
| 4,740,195 A | | 4/1988 | Lanciano |
| 4,787,892 A | | 11/1988 | Rosenberg |
| 4,867,745 A | * | 9/1989 | Patel .................... A61M 25/06 604/158 |
| 4,885,503 A | | 12/1989 | Takahashi et al. |
| 5,052,998 A | | 10/1991 | Zimmon |
| 5,074,484 A | | 12/1991 | Kray |
| 5,078,684 A | | 1/1992 | Yasuda |
| 5,213,575 A | | 5/1993 | Scotti |
| 5,224,935 A | | 7/1993 | Hollands |
| 5,308,318 A | | 5/1994 | Plassche, Jr. |
| 5,352,198 A | | 10/1994 | Goldenberg et al. |
| 5,399,165 A | | 3/1995 | Paul, Jr. |
| 5,419,764 A | | 5/1995 | Roll |
| 5,472,435 A | * | 12/1995 | Sutton ........................... 604/540 |
| 5,489,269 A | | 2/1996 | Aldrich et al. |
| 5,506,202 A | | 4/1996 | Vertesy et al. |
| 5,522,400 A | | 6/1996 | Williams |
| 5,549,331 A | | 8/1996 | Yun et al. |
| 5,666,970 A | | 9/1997 | Smith |
| 5,693,083 A | | 12/1997 | Baker et al. |
| 5,704,926 A | | 1/1998 | Sutton |
| 5,730,724 A | | 3/1998 | Plishka et al. |
| 5,730,730 A | | 3/1998 | Darling, Jr. |
| 5,806,202 A | | 9/1998 | Blackman et al. |
| 5,893,880 A | | 4/1999 | Egan et al. |
| 5,904,648 A | | 5/1999 | Arndt et al. |
| 5,941,849 A | | 8/1999 | Amos, Jr. et al. |
| 6,159,177 A | | 12/2000 | Amos et al. |
| 6,165,183 A | | 12/2000 | Kuehn et al. |
| 6,213,986 B1 | | 4/2001 | Darling, Jr. |
| 6,231,542 B1 | | 5/2001 | Amos et al. |
| 6,358,271 B1 | | 3/2002 | Egan et al. |
| 6,454,740 B1 | | 9/2002 | Mody |
| 6,508,789 B1 | | 1/2003 | Sinnott et al. |
| 6,547,761 B2 | | 4/2003 | Liu |
| 6,673,060 B1 | | 1/2004 | Fleming, III |
| 6,699,233 B2 | * | 3/2004 | Slanda ................... A61M 25/00 604/523 |
| 7,087,038 B2 | | 8/2006 | Lee |
| 7,217,256 B2 | | 5/2007 | Di Palma |
| 7,338,475 B2 | | 3/2008 | Brown |
| 7,578,814 B2 | | 8/2009 | Accisano et al. |
| 7,618,398 B2 | * | 11/2009 | Holman ................ A61F 2/0095 604/160 |
| 7,641,630 B2 | | 1/2010 | Accisano, III et al. |
| 2004/0059293 A1 | | 3/2004 | Chu et al. |
| 2005/0070821 A1 | | 3/2005 | Deal et al. |
| 2005/0107739 A1 | | 5/2005 | Palma |
| 2005/0203485 A1 | | 9/2005 | Lee |
| 2006/0129111 A1 | | 6/2006 | Mottola |
| 2006/0206096 A1 | | 9/2006 | Accisano et al. |
| 2006/0212009 A1 | | 9/2006 | Accisano et al. |
| 2006/0217667 A1 | | 9/2006 | Accisano et al. |
| 2007/0032779 A1 | | 2/2007 | Accisano et al. |
| 2007/0078385 A1 | | 4/2007 | Accisano et al. |
| 2007/0083189 A1 | | 4/2007 | Lampropoulos |

FOREIGN PATENT DOCUMENTS

| | | |
|---|---|---|
| WO | WO 03/097127 | 11/2003 |
| WO | WO 2006/098818 | 9/2006 |
| WO | WO 2006/098819 | 9/2006 |
| WO | WO 2006/101592 | 9/2006 |
| WO | WO 2007/019074 | 2/2007 |

OTHER PUBLICATIONS

Notice of Allowance dated Jun. 16, 2010 in U.S. Appl. No. 11/205,609.
Office action dated Jul. 14, 2010 in U.S. Appl. No. 12/557,348.
Notice of Allowance dated Jan. 7, 2011 in U.S. Appl. No. 12/557,348.
Notice of abandonment dated Dec. 1, 2009 in U.S. Appl. No. 11/081,301.
Notice of allowance dated Mar. 19, 2010 in U.S. Appl. No. 11/205,609.
Office action dated Jul. 20, 2009 in U.S. Appl. No. 11/205,609.
Angiodynamics, Abscession Drainage Catheter: A Quick Guide to the Locking Mechanism, AngioDynamics, Inc., Nov. 1999.
International Search Report and Written Opinion, PCT/US06/03021, mailed Sep. 18, 2007, Accisano et al.
International Search Report and Written Opinion, PCT/US06/03464, mailed Jul. 26, 2007, Accisano et al.
International Search Report and Written Opinion, PCT/US06/03467, mailed Jun. 14, 2006, Accisano et al.
International Search Report and Written Opinion, PCT/US06/29304, mailed Feb. 21, 2007, Accisano et al.
Office Action issued May 28, 2008 in co-pending U.S. Appl. No. 11/078,140.
Interview Summary issued Nov. 25, 2008 in co-pending U.S. Appl. No. 11/078,140.
Amendment and Response to Office Action filed Nov. 26, 2008 in co-pending U.S. Appl. No. 11/078,140.
Statement of Substance of Interview filed Dec. 22, 2008 in co-pending U.S. Appl. No. 11/078,140.
Final Office Action issued Mar. 3, 2009 in co-pending U.S. Appl. No. 11/078,140.
Interview Summary issued Jul. 7, 2009 in co-pending U.S. Appl. No. 11/078,140.
Amendment after Final and Request for Continued Examination filed Sep. 3, 2009 in co-pending U.S. Appl. No. 11/078,140.
Notice of Allowance issued Oct. 13, 2009 in co-pending U.S. Appl. No. 11/078,140.
Office Action issued Sep. 4, 2008 in co-pending U.S. Appl. No. 11/198,642.
Amendment and Response filed Dec. 19, 2008 in co-pending U.S. Appl. No. 11/198,642.
Interview Summary issued Dec. 23, 2008 in co-pending U.S. Appl. No. 11/198,642.
Statement of Substance of Interview filed Jan. 23, 2009 in co-pending U.S. Appl. No. 11/198,642.
Notice of Allowance issued Apr. 20, 2009 in co-pending U.S. Appl. No. 11/198,642.
Issue Notification issued Aug. 5, 2009 in co-pending U.S. Appl. No. 11/198,642.
Request for Continued Examination filed Aug. 24, 2009 in co-pending U.S. Appl. No. 11/198,642.
Final Office Action issued Mar. 10, 2009 in co-pending U.S. Appl. No. 11/081,301.
Amendment and Response filed Dec. 29, 2008 in co-pending U.S. Appl. No. 11/081,301.
Office Action issued Jun. 26, 2008 in co-pending U.S. Appl. No. 11/081,301.
Amendment filed Apr. 23, 2008 in co-pending U.S. Appl. No. 11/081,301.
Office Action issued Oct. 23, 2007 in co-pending U.S. Appl. No. 11/081,301.
Office Action issued Oct. 16, 2008 in co-pending U.S. Appl. No. 11/608,518.
Interview Summary issued Mar. 31, 2009 in co-pending U.S. Appl. No. 11/608,518.
Amendment and Response filed Apr. 16, 2009 in co-pending U.S. Appl. No. 11/608,518.
Notice of Allowance issued Jul. 27, 2009 in co-pending U.S. Appl. No. 11/608,518.
Request for Continued Examination filed Sep. 28, 2009 in co-pending U.S. Appl. No. 11/608,518.
Notice of Allowance issued Feb. 5, 2010 in co-pending U.S. Appl. No. 11/608,518.
Notice of Allowance issued Aug. 5, 2009 in co-pending U.S. Appl. No. 11/078,939.
Amendment and Response filed Mar. 10, 2009 in co-pending U.S. Appl. No. 11/078,939.
Notice of Non-Compliant Amendment issued Jan. 12, 2009 in co-pending U.S. Appl. No. 11/078,939.
Statement of Substance of Interview filed Jan. 2, 2009 in co-pending U.S. Appl. No. 11/078,939.

(56) References Cited

OTHER PUBLICATIONS

Interview Summary issued Dec. 2, 2008 in co-pending U.S. Appl. No. 11/078,939.
Proposed Amendments filed Nov. 21, 2008 in co-pending U.S. Appl. No. 11/078,939.
Office Action issued May 21, 2008 in co-pending U.S. Appl. No. 11/078,939.
Request for Continued Examination filed Nov. 5, 2009 in co-pending U.S. Appl. No. 11/078,939.
Notice of Allowance issued Jan. 26, 2010 in co-pending U.S. Appl. No. 11/078,939.

* cited by examiner

DRAINAGE CATHETER WITH PIG-TAIL STRAIGHTENER

BACKGROUND OF THE INVENTION

The present invention relates to catheters. In particular, the present invention relates to a catheter device including, a drainage catheter, at least one rigid member, such as a cannula, or a trocar, and a pig-tail straightener.

One problem often encountered in modern medicine relates to volumes of fluids that collect in a patient's tissue, body cavities, or other positions within a patient's body that exceed normal volumes. Collected fluids can contribute to infection, exert harmful pressure on the patient's organs, or otherwise impede the proper care and recovery of a patient. Drainage catheters have long been utilized to drain such excess volumes of fluids from a patient's body. Typically, the catheter is adapted to be introduced into the patient to the site where the excess fluid is accumulated. A plurality of drainage bores are positioned in the distal end of the catheter to allow passage of the fluids and any materials suspended in the fluids from the volume of fluid to the drainage bore of the catheter.

The distal end of drainage catheters are typically adapted to form an anchor configuration to secure the drainage catheter at the site where excess fluid is accumulated. However, the tissue surrounding drainage sites often does not provide a solid or reliable substrate to maintain the position of the catheter. As a result, the anchor configuration of the catheter is typically formed in a relatively large pigtail type loop that provides a reliable anchor regardless of the characteristics of the surrounding tissue. The pigtail loop is formed by curling the tip of the catheter tube such that the tip of the catheter contacts a more proximal position on the catheter tube. This is accomplished utilizing a suture that is threaded between the proximal position and the tip of the catheter. Some examples of such catheters are disclosed in U.S. patent application Ser. No. 11/205,609 filed Aug. 17, 2005 which is incorporated herein by reference. When the suture is foreshortened, the tip of the catheter is securely positioned relative to the proximal position on the catheter tube. A portion of the distal end of the catheter tube between the tip of the catheter and the proximal position where the suture exits the catheter tube forms a resulting pig-tail type loop.

The pig-tail type loop may be formed in the catheter tube such that the catheter tube is biased towards the pig-tail configuration, or the catheter tube may maintain a pig-tail type after the catheter tube has been held in position for some time. In such circumstances, it may be difficult to straighten the pig-tail for insertion or removal. Cannulas, trocars and other rigid members can be inserted into the catheter tube to straighten out the pig-tail. In some cases, the cannula, trocar, or rigid member can be difficult to fully insert because the end of the cannula, trocar, or rigid member may catch on or puncture the wall of the catheter.

One approach has been to place a sleeve, as shown in U.S. Pat. No. 4,738,667, over the catheter tube. The sleeve can slide along the length of the catheter tube to straighten the pig-tail for insertion or removal. However, these sleeves have the disadvantage of having an abrupt end, which can cause the sleeve to catch on or tear into the catheter member.

What is needed is a device that allows a practitioner to straighten a pig-tail in a catheter tube to allow for easier insertion or removal of the catheter tube while limiting or preventing damage to the catheter tube.

BRIEF SUMMARY OF AN EMBODIMENT OF THE INVENTION

The present invention relates to catheters. In particular, the present invention relates to a drainage catheter including a tube body configured to assume a pig-tail configuration in a distal end of the tube body, at least one rigid member, such as a trocar or cannula, that can be placed inside of the tube body, and a pig-tail straightener, such as a sleeve, for straightening the tube body to provide easier insertion of a rigid member into the tube body.

To insert a catheter, the practitioner may use a trocar and cannula placed inside of the tube body of the catheter to create an opening in a patient's body to accommodate the catheter, or a cannula may be placed in the tube body alone to make the catheter body more rigid. In some instances, the tube body may be made of a relatively soft and pliable material to accommodate desirable design characteristics of a catheter. The distal end of the tube body may also be biased in a pig-tail configuration to aid in anchoring the catheter in place once placed in a patient. Similarly, the tube body may become biased in a pig-tail configuration after being held in the pig-tail configuration for a period of time. In such instances, placing the cannula or trocar may be difficult or may cause damage to the wall of the tube body To place the trocar or cannula into the catheter, a pig-tail straightener, such as a sleeve member slidably placed on the outside of the catheter tube body, may be used. The sleeve member has a lip, such as a rounded end, rolled end, smoothly flanged end, or other smooth feature, to aid in sliding along and straightening the catheter tube body without catching on or damaging the outside surface of the tube body. A practitioner slides the pig-tail straightener along the tube body to the distal end of the tube body, thereby straightening any bends or pig-tail loops in the tube body. The pig-tail straightener is positioned proximate the distal end of the tube body. The rigid member is then placed inside of the tube body through the proximal end. With the rigid member in place, the pig-tail straightener may then be removed from the catheter entirely. The catheter is thus retained in an extended, rigid position.

To place the catheter, the practitioner may use the catheter with the rigid member inside of the tube body to place the distal end of the catheter at a desired location inside of a patient. In some cases, the rigid member may include a trocar that can be used to create the insertion hole in the patient. In other cases, the catheter may be placed in an existing opening by advancing the tube body with cannula over a guidewire. Once the catheter is in place, the rigid member may be removed, and the practitioner may secure the distal end of the tube body in the pig-tail configuration.

In some embodiments, once the distal end of the catheter tube is positioned in the desired location within the patient's body, the practitioner may grasp a proximal end of a suture and pull to shorten the suture, drawing the tip of the catheter tube in a curved, pig-tail position so that an anchor loop is formed in the distal end of the catheter tube body. The pig-tail prevents removal of the distal end of the catheter from the desired position in the patient, minimizing risk of injury.

In some embodiments, the lip on the pig-tail straightener sleeve may be formed such that the diameter of the lip is greater that the diameter of the sleeve body. In some embodiments, an end of the pig-tail straightener sleeve may be rounded such that it has a rounded edge on the inside and/or the outside of the sleeve. In other embodiments, the lip may include a smooth flange, or a rolled end.

As will be appreciated by those skilled in the art, a variety of types and configurations of catheters and of suture securement mechanisms can be utilized without departing from the scope and spirit of the present invention. For example, in one embodiment the securement mechanism may include a locking rotatable lever handle for securing a suture in an anchored position. In another embodiment, the pig-tail may be secured by bias in the tube body such that the distal end of the tube body is normally in the pig-tail configuration. The catheter may be a bladder catheter, or other type of conventional catheter.

These and other aspects of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF EXEMPLARY EMBODIMENTS

The present invention relates to catheters. In particular, the present invention relates to a drainage catheter including a catheter tube body configured to assume a pig-tail configuration in a distal end of the catheter tube body, at least one rigid member, such as a trocar, or cannula that can be placed inside of the catheter tube body, and a pig-tail straightener, such as a sleeve, for straightening the tube body to provide easier insertion of a rigid member into the catheter tube body.

Figure 1A:
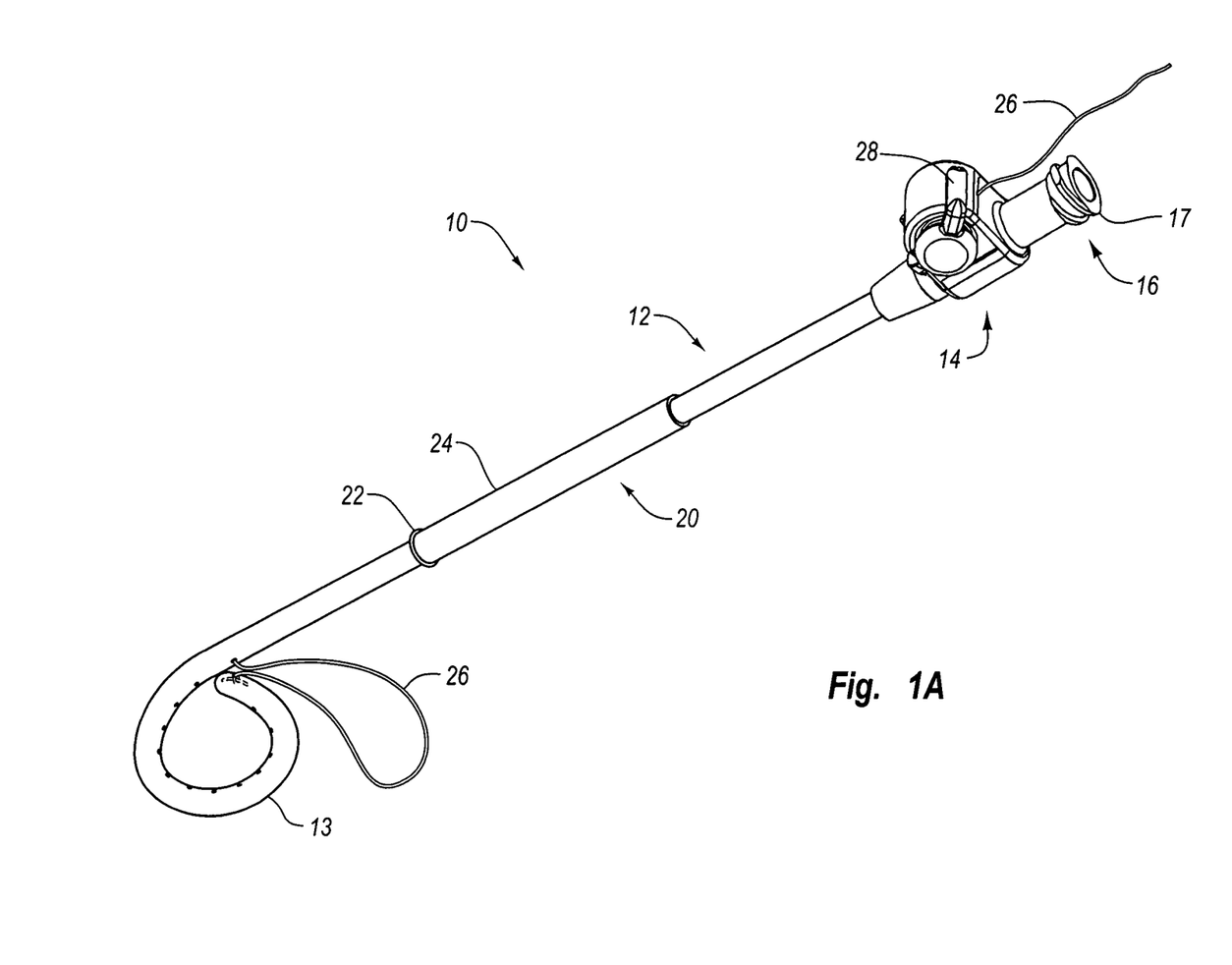
FIG. 1A is a perspective view of a drainage catheter illustrating a catheter tube body in a pig-tail configuration and a pig-tail straightener sleeve.
Figure 1B:
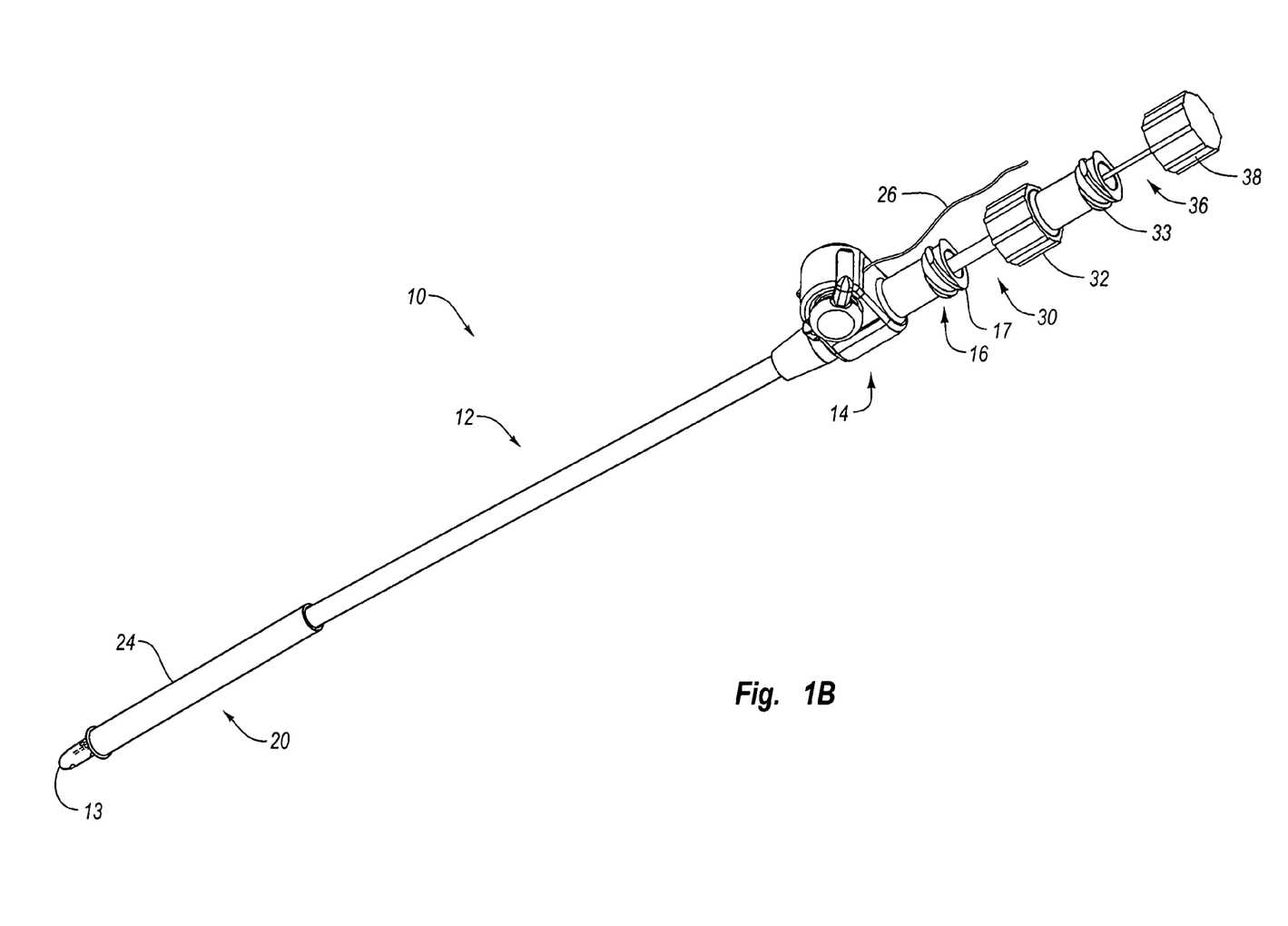
FIG. 1B is a perspective view of a drainage catheter illustrating a pig-tail straightener positioned to straighten a catheter tube body and a rigid member partially within the catheter tube body of FIG. 1A.
Figure 1C:
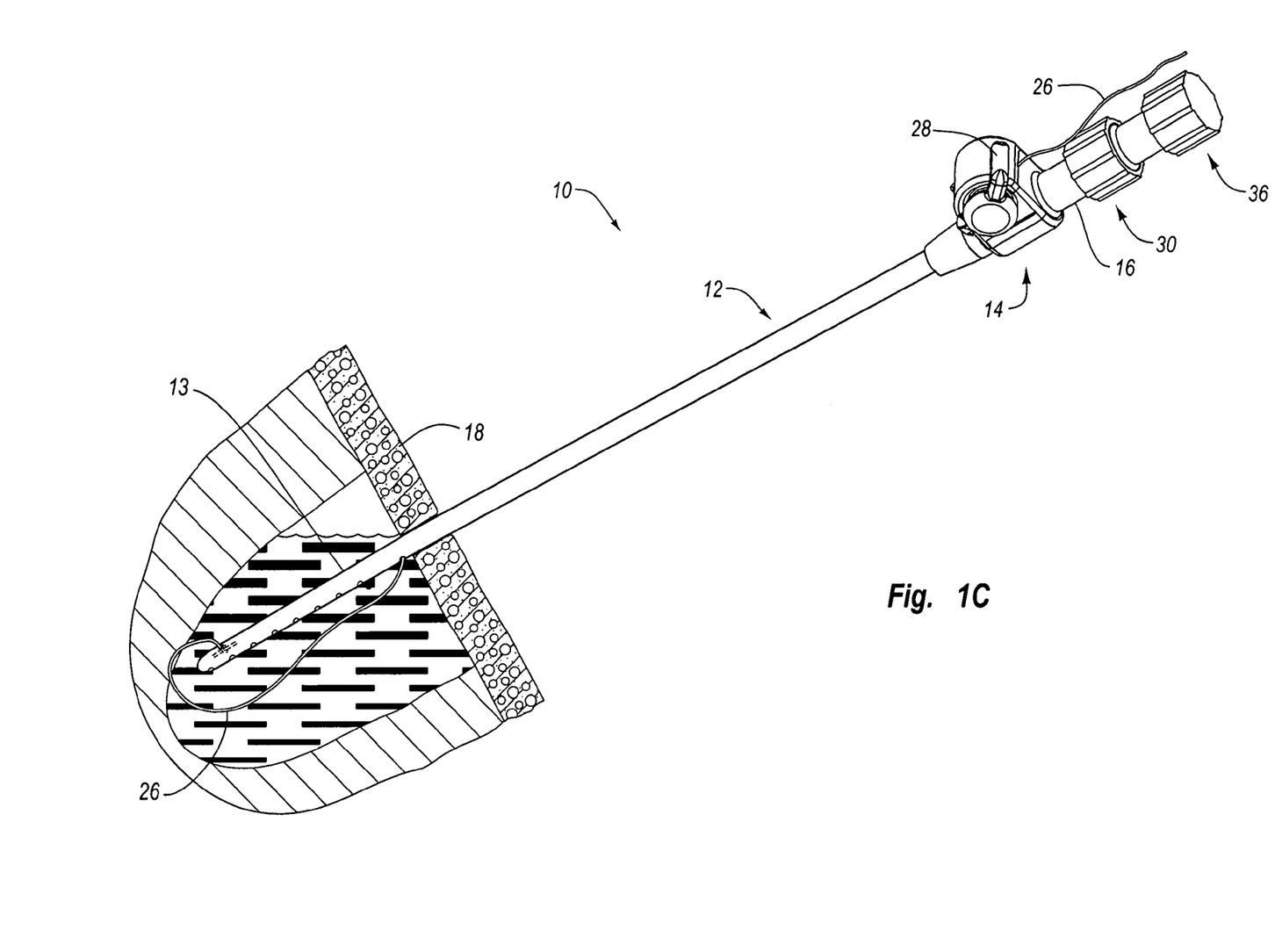
FIG. 1C is a perspective view of the drainage catheter of FIG. 1A, with rigid members and pig-tail straightener sleeve, being placed within a body with rigid members.

FIGS. 1A-1C are perspective views of drainage catheter 10 illustrating a catheter tube body 12 having a distal end 13, a proximal end 16, a locking catheter hub 14 having a rotatable lever handle 28, securement suture 26, and pig-tail straightener sleeve 20.

FIG. 1A shows distal end 13 of catheter tube body 12 in a pig-tail configuration. Pig-tail configuration may also be any loop, bend, hook, spiral, twist, or similar alteration that would secure distal end 13 of catheter 10 in a desired location. Distal end 13 may be normally biased in a pig-tail configuration, as shown in FIG. 1A, or it may be normally straight, requiring modification to a pig-tail configuration through any number of methods.

Figure 2:
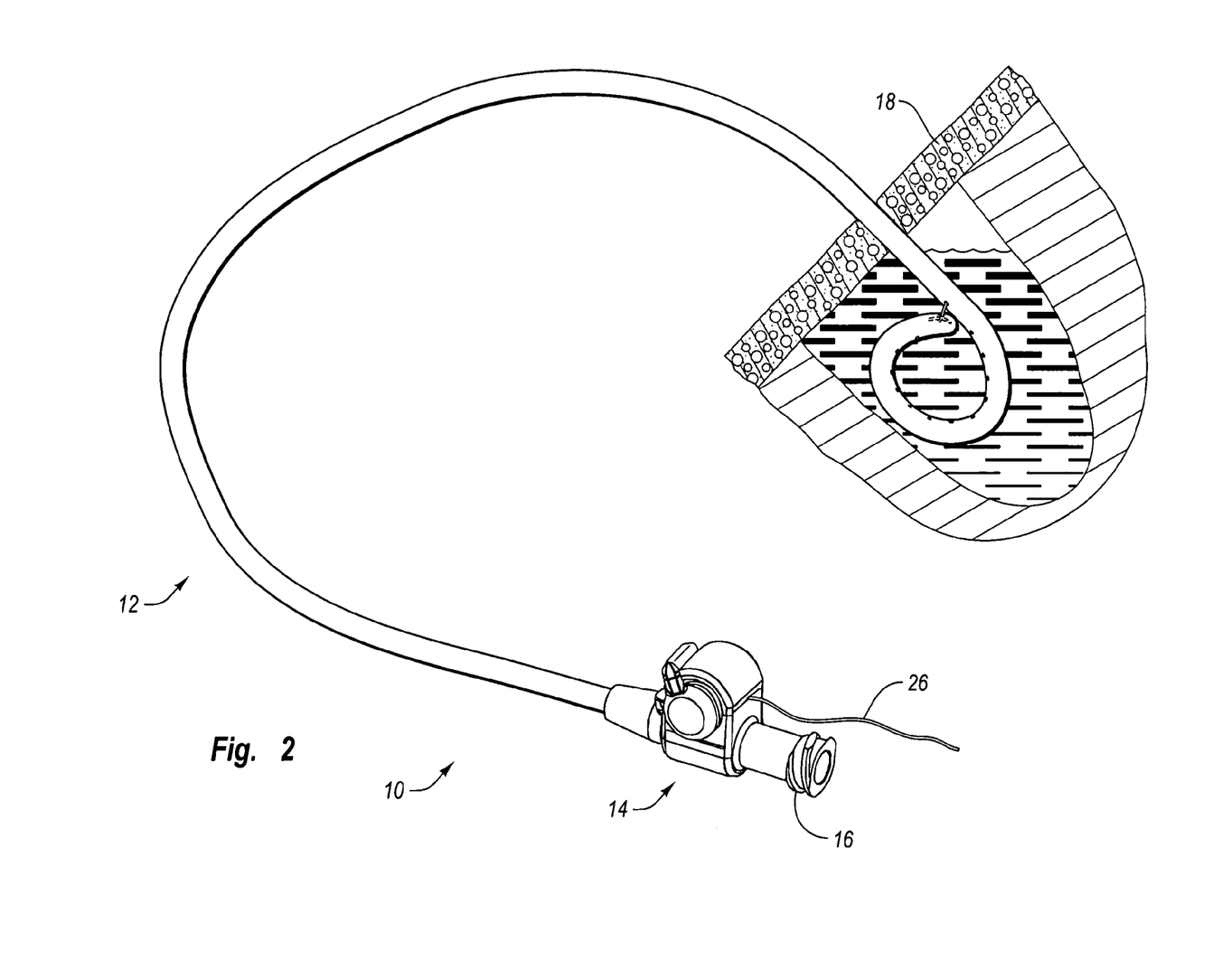
FIG. 2 is a perspective view of the drainage catheter of FIG. 1A in place and secured with a pig-tail.

In the example embodiments disclosed, drainage catheter 10 is configured to be utilized for potentially prolonged periods to drain fluid from a patient. Catheter hub 14 and rotatable lever handle 28 provide a simple and effective mechanism to allow a user to selectively implement and maintain the anchor configuration of a distal end 13 of catheter tube body 12. Rotatable lever handle 28 is adapted to secure a suture thread 26 to maintain the anchor configuration of distal end 13 of catheter tube body 12 so that the position of catheter tube body 12 is secured within a patient's body 18 (as shown in FIGS. 1C-2). The rotatable lever handle 28 has a released position for allowing movement of the suture, and a secured position for preventing movement of the suture. Rotatable lever handle 28 is shown in the released position in FIG. 1A.

To maintain the desired positioning of distal end 13 within the patient 18, the practitioner grasps the free end of suture 26 extending from catheter hub 14. The user then pulls suture 26 in a rearward direction away from distal end 13 of catheter tube body 12 such that distal end 13 forms a pig-tail type anchor configuration. The anchor loop configuration in distal end 13 of catheter tube body 12 maintains the position of distal end 13 in patient 18, even where the wall of a body cavity is insufficiently rigid to secure traditional catheter securement devices.

Typically, once distal end 13 of catheter tube body 12 is positioned in the pig-tail configuration, the drainage catheter 10 will remain positioned within the body of the patient for a considerable period of time to facilitate ongoing drainage of the volume of bodily fluid from the patient.

In the illustrated embodiment, locking catheter hub 14 is utilized in connection with catheter tube body 12 of drainage catheter 10. Catheter tube body 12 comprises an elongate tubular member having a drainage lumen for allowing the fluid to exit patient 18, through the distal end 13 of catheter tube body 12. The configuration of catheter tube body 12 allows fluids to be drained from a patient 18 through drainage catheter 10, exiting at proximal end 16.

Figure 3A:
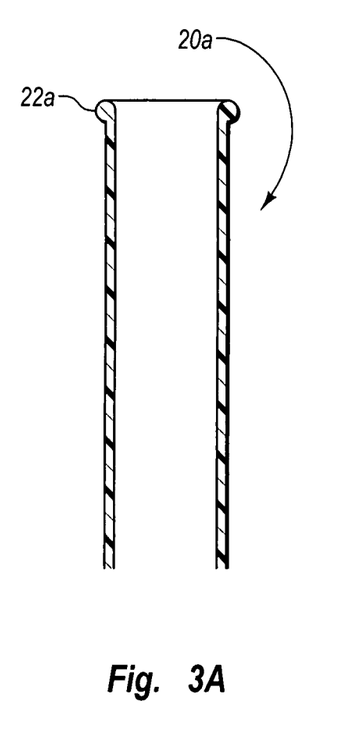
FIG. 3A is a cross-sectional view of an embodiment of a pig-tail straightener.
Figure 3B:
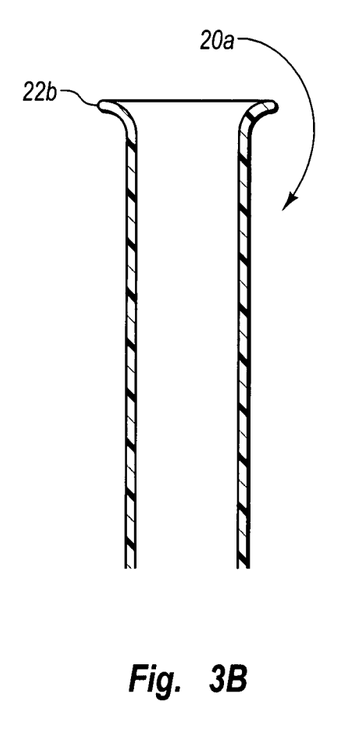
FIG. 3B is a cross-sectional view of an embodiment of a pig-tail straightener.
Figure 3C:
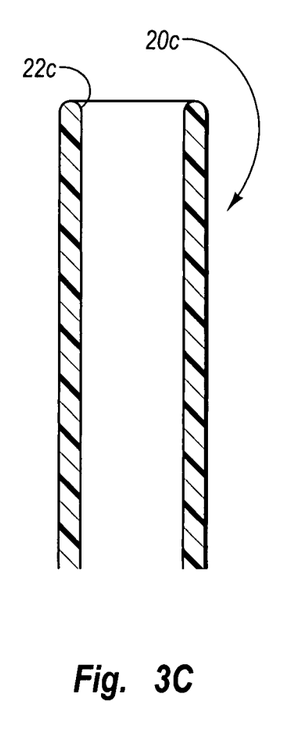
FIG. 3C is a cross-sectional view of an embodiment of a pig-tail straightener.

Pig-tail straightener 20 may have a sleeve body 24 slidably engaged with catheter tube body 12. Pig-tail straightener 20 may be a sleeve or tube having an inner diameter larger than the outer diameter of catheter tube body 12, allowing pig-tail straightener 20 to slide along the length of catheter tube body 12. Pig-tail straightener 20 includes lip 22 to facilitate sliding pig-tail straightener 20 from a proximal location near hub 14, as illustrated in FIG. 1A, to a distal location covering, at least in part, distal end 13 of catheter tube body 12. Lip 22 may be a raised ring around one end of pig-tail straightener 20, as illustrated in FIGS. 1A-1C, 3A-3B such that lip 22 has a diameter greater than the diameter of sleeve body 24. Alternatively, lip 22 may be a rounding of the distal end of sleeve body 24 such that a smooth edge is presented, as shown in FIGS. 3A-3C. In FIG. 3A, lip 22a is a rounded projection extending from sleeve body 24a, such that lip 22a has a diameter greater than the diameter of sleeve body 24a. In FIG. 3B, lip 22b is a gradually expanding projection extending from sleeve body 24b, such that lip 22b has a diameter greater than the diameter of sleeve body 24b. In FIG. 3C, sleeve body 24c has thick walls allowing lip 22a to have a rounded end. In other embodiments, the lip may include a rounded end formed on the gradually expanding projection extended from the sleeve body.

As pig-tail straightener 20 is moved distally, lip 22 engages distal end 13, straightening the pig-tail to a straight configuration, as illustrated in FIG. 1B. Lip 22 is sufficiently rounded or smooth to slide along catheter tube body 12 rather than catching on or damaging catheter tube body 12. Once the catheter tube body 12 is in a straightened configuration, as shown for example in FIG. 1B, the catheter tube body may then be prepared to be introduced into a patient, as shown in FIG. 1C.

Distal end 13 is introduced into patient 18 at a position configured to optimize the drainage of fluid from patient 18. To facilitate the correct positioning of drainage catheter 10, distal end 13 can be introduced into patient 18 through an existing lumen, or made rigid by insertion of one or more rigid members 30, 36 into the lumen of catheter tube body 12. In this example embodiment, cannula 30 can be attached to drainage catheter 10 by engaging a threaded connecting member 17 at proximal end 16 with threaded end 32 of cannula 30. As illustrated in FIGS. 1B-1C, cannula 30 may be attached at one end to proximal end 16 of catheter tube body 12. Trocar 36 may also be introduced into catheter tube body 12 to allow drainage catheter 10 to be inserted directly into the patient 18 through an opening created by a sharp end of trocar 36.

Cannula 30 may have a blunt end and a lumen to allow passage of trocar 36 through cannula 30 and catheter tube body 12, creating a nested arrangement, as illustrated in FIGS. 1B-1C. Cannula 30 may have a threaded portion 33 to releasably engage threaded end 38 of trocar 36. Cannula 30 and trocar 36 may be the approximate length of catheter tube body 12 and contained entirely or substantially by catheter tube body 12.

With pig-tail straightener 20 in place over distal end 13, cannula 30 and/or trocar 36 may be inserted into catheter tube body 12 without catching on, puncturing, or otherwise damaging catheter tube body 12 with the distal end of cannula 30 or the sharp distal end of trocar 36.

As illustrated in FIG. 1C, drainage catheter 10 may be inserted into patient 18 with both cannula 30 and trocar 36 in place within catheter tube body 12. Alternatively, cannula 30 may be employed separately as may be expedient to a practitioner. Some embodiments of cannula 30 may be made of plastic, metal, or other appropriate material, and may have varying degrees of rigidity, depending on the required application.

As illustrated in FIG. 2, pig-tail straightener 20 is removed from catheter tube body 12 after insertion of rigid members 30, 36 and prior to placement of drainage catheter 10 in patient 18 by sliding pig-tail straightener off of distal end 13 of catheter tube body 12 and discarded as appropriate.

As will be appreciated by those skilled in the art, a variety of types and configurations of catheters can be utilized for draining bodily fluids from a patient without departing from the scope and spirit of the present invention. For example, in one embodiment, the fluids to be drained exit from a portion of the drainage catheter other than the catheter hub. In another embodiment, the drainage catheter 10 is adapted to be positioned adjacent an organ or in the vasculature of the patient. In another embodiment, the drainage catheter 10 is introduced utilizing a guidewire or rigid stylet.

In some embodiments, a kit according to the present invention may include, in addition to the components discussed above, additional tubing, sterile gloves, sterilization pads, additional members configured to be inserted into the drainage catheter such as diagnostic testing implements or devices, structural support elements, or other devices and implements used in conjunction with drainage catheters.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A drainage catheter for use in providing a fluid pathway for draining bodily fluid from a cavity or tissue of a patient, the drainage catheter being configured such that a suture utilized in connection with the drainage catheter selectively secures the distal end of the catheter in an anchor configuration, the drainage catheter comprising:

a catheter tube having a proximal end and a distal end, the distal end of the catheter tube being configured to be positioned in tissue, cavity, or other location within the body of the patient having an amount of fluid to be drained, the catheter tube comprising a distal end portion comprising a continuously decreasing outside diameter along a longitudinal direction to the distal end;

a suture running the length of at least a portion of the catheter tube and being secured to the distal end of the catheter tube to selectively maintain the anchor configuration of the distal end of the catheter;

a catheter hub coupled to the proximal end of the catheter tube, the catheter hub being configured to secure the suture to maintain the anchor configuration of the distal end of the catheter and release the suture to release the anchor configuration of the distal end of the catheter; and a fixed-diameter sleeve configured to move axially along the catheter tube without requiring rotational movement of the sleeve, the sleeve being adapted to slide over the distal end of the catheter tube thereby straightening the catheter tube from a curved configuration into a straight configuration such that a rigid elongate member may be placed inside of the catheter to straighten the distal end of the catheter so as to facilitate the introduction or removal of the catheter relative to the patient, wherein the rigid elongate member is at least one of a cannula or a trocar; the sleeve further comprising lip disposed on a distal end of the sleeve, wherein the lip:

extends circumferentially around the longitudinal axis of the drainage catheter;

has a greater external diameter than an external diameter of a portion of the sleeve immediately proximal of the lip;

presents a smooth, rounded surface that extends from the most distal portion of the lip to the most lateral portion of the lip, wherein the most distal portion of the lip and the most lateral portion of the lip are different portions; and facilitates movement of the catheter tube proximally with respect to the sleeve by presenting a smooth interface between the sleeve and the catheter tube; and wherein the sleeve is removable from the catheter by distal displacement of the sleeve beyond the distal end of the catheter.

2. The drainage catheter of claim 1, wherein the distal end of the tube body is configured to be secured in a pig-tail position.

3. The drainage catheter of claim 1, wherein the tube body is at least partially biased into a pig-tail position.

4. The drainage catheter of claim 1, wherein the tube body is a soft, pliable material.

5. The drainage catheter of claim 1, wherein the lip includes a rounded portion on the inside of the sleeve.

6. The drainage catheter of claim 1, wherein the lip comprises a gradually expanding projection extending from the sleeve such that a portion of the lip has a greater inside diameter than the sleeve.

7. A catheter kit having drainage catheter for use in providing a fluid pathway for draining bodily fluid from a cavity or tissue of a patient, the drainage catheter being configured such that a suture utilized in connection with the drainage catheter selectively secures the distal end of the catheter in an anchor configuration, the catheter kit comprising:

a drainage catheter, the drainage catheter including:
        a catheter tube having a proximal end and a distal end, the distal end of the catheter tube being configured to be positioned in tissue, cavity, or other location within the body of the patient having an amount of fluid to be drained, the distal end of the catheter tube comprising a non-flaring end;
        a suture running the length of at least a portion of the catheter tube and being secured to the distal end of the catheter tube to selectively maintain the anchor configuration of the distal end of the catheter;
        a catheter hub coupled to the proximal end of the catheter tube, the catheter hub being configured to secure the suture to maintain the anchor configuration of the distal end of the catheter and release the suture to release the anchor configuration of the distal end of the catheter;
    at least two elongate rigid members such as a cannula or trocar, the at least two elongate rigid members, each of the at least two elongate rigid members being configured to be slidably received within the tube; and
    a fixed-diameter sleeve configured to move axially along the catheter tube, the sleeve being adapted to slide over the distal end of the catheter tube thereby straightening the catheter tube from a curved configuration into a straight configuration to facilitate entry of at least one of the two elongate rigid members inside of the catheter tube to straighten the distal end of the catheter allowing a distal portion of one or both of the at least two elongate rigid members to extend to the distal end of the catheter tube without catching or damaging the distal portion of the catheter tube and to allow the introduction or removal of the catheter relative to the patient, the sleeve further comprising a lip disposed on an distal end of the sleeve, wherein the lip:
        extends circumferentially around the longitudinal axis of the drainage catheter;
        has a greater external diameter than an external diameter of a portion of the sleeve immediately proximal of the lip;
        presents a smooth, rounded surface that extends from the most distal portion of the lip to the most lateral portion of the lip, wherein the most distal portion of the lip and the most lateral portion of the lip are different portions; and
        facilitates movement of the catheter tube proximally with respect to the sleeve by presenting a smooth interface between the sleeve and the catheter tube, and
    wherein the sleeve is removable from the catheter by distal displacement of the sleeve beyond the distal end of the catheter.

8. The catheter kit of claim 7, wherein at least one of the at least two rigid members is configured to rotatably attach to the catheter hub.

9. The catheter kit of claim 7, wherein the sleeve is configured to slidably engage the tube such that the sleeve slides along an exterior surface of the tube.

10. The catheter kit of claim 7, wherein the lip is configured to be oriented toward a distal, curved end of the tube.

11. The catheter kit of claim 7, wherein the at least two rigid members are configured to be inserted simultaneously within the tube.

12. The catheter kit of claim 11, wherein one of the at least two rigid members is configured to be placed within the other rigid member.

13. The catheter kit of claim 7, wherein the lip comprises a gradually expanding projection extending from the sleeve such that a portion of the lip has a greater inside diameter than the sleeve.

\* \* \* \* \*

UNITED STATES PATENT AND TRADEMARK OFFICE
CERTIFICATE OF CORRECTION

PATENT NO.         : 9,233,226 B2
APPLICATION NO.    : 11/507777
DATED              : January 12, 2016
INVENTOR(S)        : Fred P. Lampropoulos et al.

It is certified that error appears in the above-identified patent and that said Letters Patent is hereby corrected as shown below:

In the Claims:

Column 6, Claim 1, Line 35 reads, ". . . sleeve further comprising lip disposed . . .", which should read ". . . sleeve further comprising a lip disposed . . ."

Column 6, Claim 7, Line 66 reads, ". . . kit having drainage catheter for use . . .", which should read "kit having a drainage catheter for use . . ."

Column 7, Claim 7, Line 24 reads, ". . . trocar, the at least two elongate rigid members, each . . .", which should read ". . . trocar, each . . ."

Column 8, Claim 7, Line 2 reads, ". . . lip disposed on an distal end . . .", which should read ". . . lip disposed on a distal end . . ."

Signed and Sealed this
Thirty-first Day of May, 2016

Michelle K. Lee
*Director of the United States Patent and Trademark Office*